(12) United States Patent
Lee et al.

(10) Patent No.: US 9,700,888 B1
(45) Date of Patent: Jul. 11, 2017

(54) POINT OF CARE MEDICAL DEVICE FOR DETECTING INFECTIOUS DISEASES

(71) Applicant: IPMD INC., Albany, CA (US)

(72) Inventors: Min Lee, Albany, CA (US); Seok Yong Moon, Seoul (KR); Matthew Lee, Albany, CA (US); Rimma Ten, Seoul (KR); Nick Huntington, Concord, CA (US); Nupur Raychaudhuri, Ann Arbor, MI (US); Phillip Scott Alexander, Indianapolis, IN (US); Laurence Bianchini, San Leandro, CA (US)

(73) Assignee: IPMD INC., Albany, CA (US)

( * ) Notice: Subject to any disclaimer, the term of this patent is extended or adjusted under 35 U.S.C. 154(b) by 0 days.

(21) Appl. No.: 15/098,105

(22) Filed: Apr. 13, 2016

(51) Int. Cl.
*B01L 3/00* (2006.01)
*C12Q 1/68* (2006.01)

(52) U.S. Cl.
CPC ..... *B01L 3/502707* (2013.01); *B01L 3/50273* (2013.01); *B01L 3/502715* (2013.01); *C12Q 1/686* (2013.01); *B01L 2200/12* (2013.01); *B01L 2300/0809* (2013.01); *B01L 2300/0832* (2013.01); *B01L 2300/0864* (2013.01); *B01L 2300/12* (2013.01); *B01L 2300/161* (2013.01); *B01L 2300/165* (2013.01); *B01L 2400/04* (2013.01); *B01L 2400/0403* (2013.01); *B01L 2400/0457* (2013.01)

(58) Field of Classification Search
CPC ......... B01L 2300/0864; B01L 2400/04; B01L 2400/0403; B01L 3/50273
See application file for complete search history.

(56) References Cited

U.S. PATENT DOCUMENTS

| | | | |
|---|---|---|---|
| 2005/0037508 A1* | 2/2005 | Hernandez | B01L 3/5027 436/163 |
| 2007/0025875 A1* | 2/2007 | Peters | B01L 3/502723 422/400 |
| 2007/0280856 A1* | 12/2007 | Ulmanella | B01L 3/502723 422/400 |

(Continued)

OTHER PUBLICATIONS

Elveflow Plug and Play Microfluidics; Microfluidics and microluidic devices: A review; http://www.elveflow.com/microfluidic-tutorials/microfluidic-reviews-and-tutorials/microfluidics-and-microfluidic-device-a-review/; 14 pages.

(Continued)

*Primary Examiner* — Jonathan Hurst
(74) *Attorney, Agent, or Firm* — Erik Birkeneder; Nixon Peabody LLP

(57) ABSTRACT

Disclosed is a microfluidic cartridge that can perform highly accurate lab quality DNA tests and other amplification based tests at the point of care. The cartridge may have slanted channels that angle downward from the inlet well, where the sample is deposited, to the reaction well, where the sample will flow down to and initiate the reaction. In some examples, the cartridge may be fabricated from specific materials that enhance passive flow through the channels. Additionally, the reaction wells have an access port that allows ventilation to the reaction wells that enhances the flow of the sample from the inlet to the reaction well. The access ports allow convenient access for depositing the reaction mixture into the reaction wells after the cartridge is fabricated.

17 Claims, 10 Drawing Sheets

(56) References Cited

U.S. PATENT DOCUMENTS

2009/0023610 A1* 1/2009 Peytavi ................ B01L 3/5027
  506/39
2010/0255483 A1* 10/2010 Ishii .................... B01L 3/50273
  435/287.2

OTHER PUBLICATIONS

Dimov, et al., Paper: Stand-alone self powered integrated microfluidic blood analysis system (SIMBAS); Lab on a Chip; 2011; 11; first published online Dec. 8, 2010; abstract; http://pubs.rsc.org/en/Content/ArticleLanding/2011/LC/c0lc00403k#!divAbstract.

* cited by examiner

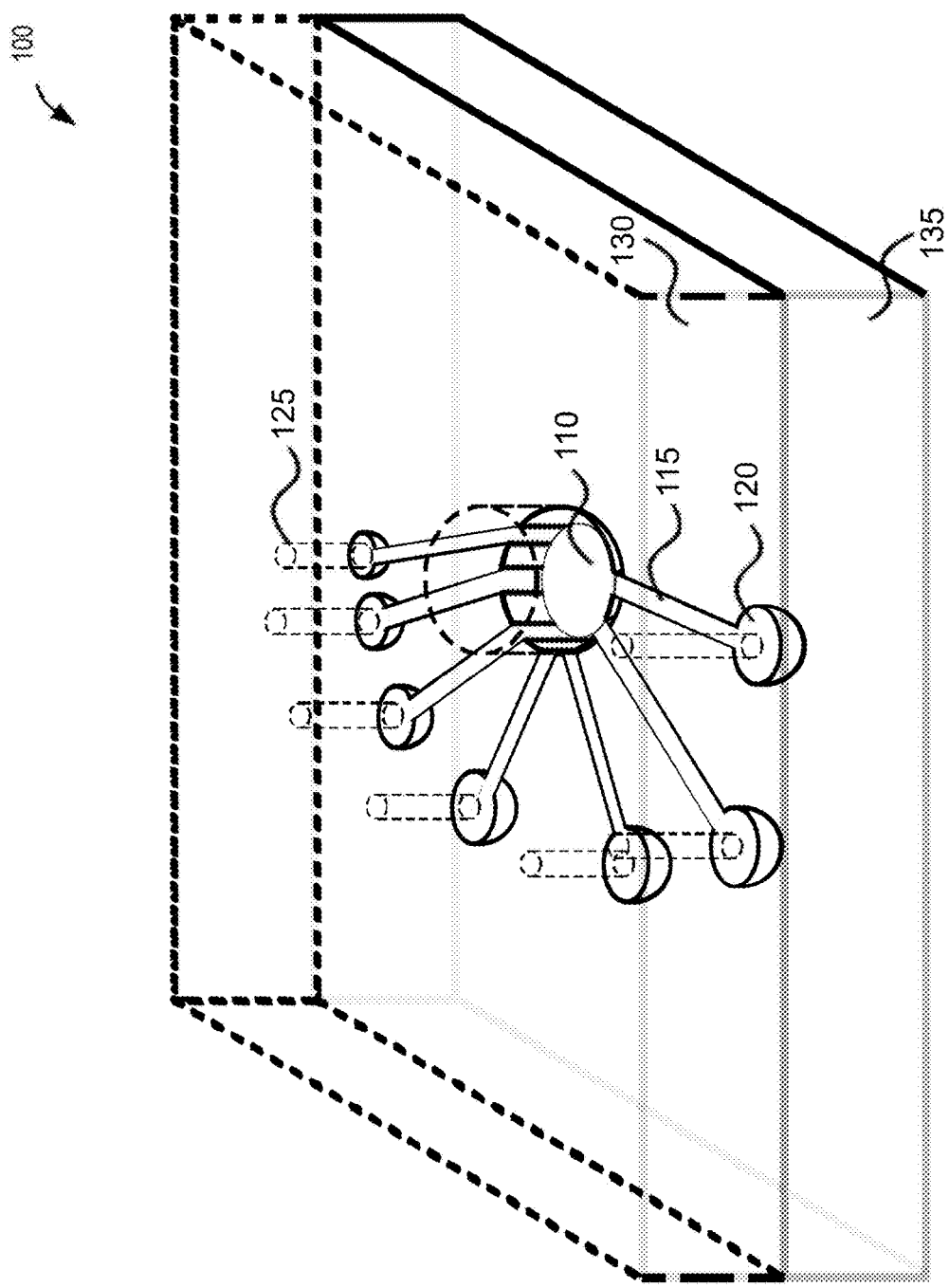

POINT OF CARE MEDICAL DEVICE FOR DETECTING INFECTIOUS DISEASES

FIELD

The present invention is directed to point of care testing microfluidic devices.

BACKGROUND

The following description includes information that may be useful in understanding the present invention. It is not an admission that any of the information provided herein is prior art or relevant to the presently claimed invention, or that any publication specifically or implicitly referenced is prior art.

In the 1980s, various groups began attempting to decentralize the lab and hospital system. Particularly, the semiconductor industry originally developed the early stage concepts of microfluidic and microfluidic devices (the so called "lab on a chip").

The use of silicon etching procedures, developed for microelectronics industry, allowed the manufacture of the first device containing mechanical micro-elements integrated on a silicon wafer. These new types of devices called MEMS (Micro Electro Mechanical Systems) gave rise to industrial applications, particularly in the field of pressure sensors, printer heads, and other micro engineering applications.

In the 1990s, applications of MEMS in the biology, chemistry, and biomedical fields evolved. A major research effort was made to develop laboratories on a chip to enable the integration of almost all the processes required for complete biological, chemical and biomedical protocols on a single microfluidic chip. At that time, the majority of microfluidic devices were still made of silicon or glass, and thus, required the heavy infrastructure of microelectronics industry. http://www.elveflow.com/microfluidic-tutorials/microfluidic-reviews-and-tutorials/microfluidics-and-microfluidic-device-a-review/

Therefore since 1990s, polymers such as a PDMS based disposable microfluidic chip/cartridges have been developed. PDMS could be manufactured by the soft lithography process. Accordingly, PDMS based microfluidic chip/cartridges were much preferred by researchers in academia since it was easier and faster to manufacture the prototypes than the traditional polymer injection molding process. Also the soft lithography process used to manufacture the PDMS chip is much more sophisticated than other methods. Thus, the MEMS could be made with components on the nanoscale to save significant amount of human samples, buffer solutions, reaction mix, primers, etc.

However, a PDMS based microfluidic chip has major drawbacks. For instance, the manufacturing process is labor intensive, and is difficult to mass produce. This makes the total manufacturing cost of a disposable chip relatively expensive at the commercialization phase.

SUMMARY

Accordingly, the inventors have identified a need for a point of care diagnostic microfluidic device that can be manufactured easily, and can be operated efficiently and effectively. Accordingly, the inventors have investigated several types of systems, types of materials for microfluidic devices for point of care diagnostic assays.

The inventors have determined that some of the key features relevant will be (1) the type of material used for a microfluidic device, and (2) the mechanism for flow management. These two features are most important because they determine: the steps and complexity of manufacturing, flow rates and behavior, cost, the number of components necessary, the size of the device(s), the complexity of operation, potential error rates or accuracy, and other features. Additionally, the flow mechanism and type of material interact to determine the flow rates and effectiveness of delivering the sample or control to the reaction area of the microfluidic device.

Flow Management

Accordingly, the inventors have determined that one of the keys to a successful point of care microfluidic cartridge is an effective system for delivery fluid form the inlet ports through the micro channels to the destination (e.g. the reaction wells) in the microfluidic devices. Microfluidic cartridges are closed systems that mimic clean room environment to avoid contamination when operated outside of centralized hospital and laboratory systems. Accordingly, the microfluidic device must be primarily closed off, with generally only an opening for a sample to be deposited and few others. Therefore, the microfluidic device needs to transport the sample through closed channels that are not open to the outside. An effective system will minimize the time of travel and be precise enough for diagnostic or other desired reactions. Additionally, the minimization of costs for associated devices and extra automation is also desirable. Accordingly, the microfluidic cartridge must be able to effectively move fluid from the sample wells to the reaction wells.

In the past, researchers have attempted various systems to assist in the movement of the fluids, including active flow control devices that are external to the microfluidic devices. For instance, researchers have installed flow control devices include pumps, syringe pumps, and others. However, these devices require extra power, tubing, space, and therefore are not amenable to a point of care setting with minimal oversight and equipment support. For instance, if a pump is utilized, the pump will have to be connected and installed, making the operation of the device more complicated, and requiring more training. Also, this will increase the expense of the device, and make it more difficult to deploy several of these devices at many remote clinics.

Thus, researchers then developed passive systems that drive the flow of the liquid through the microfluidic devices. For instance, some researchers have developed passive microfluidic cartridges using vacuums. However, the surface tension and internal pressure make the passive advance of the fluid inside the systems relatively slow. For instance, the fastest devices generally take about 90 minutes for the liquids to advance from the input port to the reaction area. http://pubs.rsc.org/en/Content/ArticleLanding/2011/LC/c01c00403k#!divAbstract. Also, the shelf life of vacuum treated cartridges is limited, which reduces the commercialization potential.

Other researchers developed methods using paper or other materials to assist in the flow using capillary action. However, these methods are more complicated to manufacture, and generally require larger channels and potentially prone to contamination, dilution or filtration of the liquids. Accordingly, these methods are not ideal.

Type of Material

The material of the microfluidic cartridge will determine its natural flow dynamics, including the amount of surface tension is created in the channels of the microfluidic cartridge. Accordingly, by manipulating the surface topography, hydrophobicity, and other characteristics of the material the flow dynamics may be optimized for a particular application.

For instance, without any extra assistance PMMA based cartridges have shown to have relatively high surface tension—at least using certain diameter/cross sectional area of channels. Therefore, different materials or mechanisms may be investigated for optimizing flow rates.

Overview

Therefore, the inventors developed an innovative disposable microfluidic cartridge. In one example, the cartridge can be used either for PCR, LAMP, or other amplification based processes for nucleic acid based detection applications. In some examples, the microfluidic cartridge uses network channels that are angled downwards towards the reaction wells from the inlet ports. Accordingly, once a sample is delivered into the inlet wells, gravity will pull the sample at a downward angle towards the reaction wells and eventually enter the reactions wells.

Additionally, inventors made small (e.g., 0.5 mm or less) ventilation holes on top of each reaction wells so that this tiny airflow actually assists in pulling the liquid sample from the inlet well to the reactions wells.

These vent holes also provide an opening to allow a technology to prefill reaction mix and primer sets in powder forms as well before packing to ship to the destinations. Fortunately, this will allow relatively low trained technicians to prefill the reaction wells and operate the device.

Furthermore, the inventors have identified certain materials that optimize the flow at certain diameters. For instance, the inventors have performed experiments with Digital ABS (RGD5160-DM), a compound similar to the ABS thermoplastic family from Object Inc., a 3D printer company. The material is named a digital material because it is made from mixing RGD535 and RGD515. RGD525 has a heat deflection temperature of 58-68° C., or 92-95° C. if curing. RGD515 has a melting point of 160° C.

This Digital ABS compound showed to be adapted for the microfluidic device because of its hydrophilic properties, contrary to PMMA that needs additional processes to change the natural hydrophobic surface into a hydrophilic surface. Also Digital ABS compound is much more porous than PMMA which also helps to reduce the surface tension.

Accordingly, in some examples the angled channels can be utilized with PMMA, or the digital ABS compounds described above or the Digital ABS compounds described above can be utilized with our without angled channels. In some examples, the flow characteristics of certain materials will allow for sufficient flow in the microfluidic channels so that angled channels are not necessary. In those cases, the pressure from the sample or liquid column inside the inlet well may be sufficient.

In some examples, the bottom half of the cartridge will be manufactured from digital ABS compounds and the top half will be manufactured from PMMA. In other examples, the top and bottom will be manufactured from PMMA and the inlet wells, channels and wells will be coated with a Digital ABS resin. In other embodiments, the inlet wells and channels will be coated with a Digital ABS resin but the reaction wells will not. Accordingly, embodiments where the top and bottom of the cartridge are made from PMMA may provide better heat resistance for the entire cartridge, but allow optimal flow characteristics. In some examples, the top and bottom portion of the channels will be coated with a Digital ABS resin.

The present invention provides a disposable microfluidic cartridge that comprises a plurality of inlet wells for injecting biological samples, a plurality of reaction wells for extracting nucleic acids from the biological samples, said reaction wells are connected to said inlet wells by a plurality of tilted channels for delivering the sample; a plurality of ventilation holes for injecting reaction mix and primers, said ventilation holes are placed on top of each reaction wells.

In one embodiment, the microfluidic cartridge comprises a top substrate and a bottom substrate. A plurality of inlet wells and ventilation holes may be formed in the upper layer of the microfluidic cartridge. Each inlet well is configured to receive a sample, and is in fluid communication with a plurality of the network channels. In some examples, each inlet well may 9.2 mm in diameter in the top layer, and 7 mm in the bottom layer of the microfluidic cartridge, 3 mm deep. In other embodiments, the inlet well may be 4 mm deep, 5 mm deep, or 6 mm deep.

The volume of each inlet well in the spans the top and bottom layers of the microfluidic cartridge can be 199.43 uL×19.24 uL. To prevent overflowing of the sample during application to the cartridge, a tube or cap may be added to the inlet well. This may have dual purposes (1) to prevent overflowing and (2) to add further gravitational force to the liquid to force it through the channels and into the reaction wells. For instance, a tygon tube could be added to the inlet well that is greater than 12 mm, for instance 13 mm.

In some examples, the ventilation holes on the upper layer of the microfluidic cartridge may be placed so they are positioned directly over the reaction wells when the upper layer and the lower layer of the microfluidic cartridge are bonded together. This allows the air to pull (or air pressure to not impede) the liquid sample from the inlet well to the reaction wells, thus providing the smooth and faster sample flow.

The vent holes of the present invention are also configured to allow access to the reaction well for pre-filling. For instance, a manufacturer may prefill the reaction mix and primers through these holes that are directly over the reaction wells before final packaging—rather than prior systems where highly trained technicians perform this reaction preparation procedure before they are applying final samples into the inlet wells, or prior to fabrication of the (which may destroy or disturb the reaction mixture during the bonding process of the microfluidic cartridge).

For instance, in prior devices, a highly trained technician would be required that would have to prepare the reaction mixtures, and primers outside of the cartridge and insert them in the inlet wells prior to depositing the samples. Accordingly, this method required highly skilled and expensive labor, and is much more prone to error. Thus, the inventors have discovered if the reaction mixtures are pre-deposited in powder form after fabrication of the cartridge through the access ports, then highly skilled labor is not required. Rather, low skilled technicians may simply deposit the samples and control solutions into the cartridge, without requiring complex reactions to be performed with the primers, etc.

These problems are critical at the point of care testing, and the present invention provides a new method to solve the above mentioned issues by using the ventilation holes for prefilling the reaction mix and primers which flow directly to the reaction wells. The vent holes may be very small and in some examples may be 0.5 mm or less in diameter in order to prevent contamination from outside.

A plurality of network channels and reaction wells may be formed in the lower layer of the microfluidic cartridge. The number of network channels (e.g., eighteen) corresponds to the number of reaction wells (e.g., eighteen). The network channels are in fluid communication with the reaction wells. In some examples, the slope of each channel prevents the backflow of the sample and ensures the sample from the inlet wells flows to the reaction well. Other features, such as gravitational force, can also enhance the sample flow from the inlet to reaction area.

In some examples, the reaction wells of the present invention may be a conical shape, cone shaped, rectangular, cylindrical or other suitable shapes. In one example, the diameter of each reaction well is 3 mm with a height 2.34 mm, and the total volume about 16.54 uL. In some examples, each reaction well can receive approximately 20 ul of the reaction mix and primers. This fluid may contain the DNA samples from the patients for the detection of the target infectious diseases.

To prevent cross-contamination of the adjacent inlet wells while applying the sample to the microfluidic cartridge and overflowing the sample, each inlet well may incorporate flexible tubing or other tubing (e.g. Tygon tube) or cap that can sit tightly in each inlet wells. For example, inlet wells with Tygon tubes may be inserted with a secure fit into the inlet wells. In one example, the diameter of each inlet well in the upper layer and the bottom layer of the microfluidic cartridge is 9.2 mm and 7 mm deep, and in some examples, the diameter of a tygon tube inserted into the inlet well may be 6.35 mm.

The biological samples that may be applied to the inlet wells of the present invention are but not limited to: (1) sputum, (2) blood, (3) urine, (4) sweat, (5) swab, and other samples from a variety of sources. In some embodiments, only the sample may be sputum and blood from, from example, a pricked finger. In some embodiments, the human sample may be injected via said inlet wells using a pipette or other suitable device.

In some examples, the microfluidic cartridge is 80 mm×80 mm in size and can incorporate three (3) separate inlet wells (1st inlet is designated for patient sample, and second inlet is for positive control, and the 3rd inlet is for negative control), said each separate inlet well is in fluid communication with eighteen (18) tilted channels with eighteen (18) reaction wells disposed on each opposite ends of said tilted channel, which makes a total of fifty-four (54) channels. This concept is not limited to 54 channels. Additional channels with various shapes and design can be implemented both of which are contemplated within the scope of the present disclosure. In this example, the 18 reaction wells per inlet well is designed for detecting 6 targets, each target has 3 reaction wells so that the reaction of each wells of the 3 wells can be compared to eliminate errors in the detection.

In some examples, the length of each network channel is 20 mm, the width 0.5 mm, and the depth of the slope area is 1.5 mm. In this example, the volume of each network channel is approximately 9.17 uL.

The device can be made from glass or polymers, such as poly (methyl methacrylate) (PMMA) and others disclosed herein. The microfluidic cartridge of the present invention may be formed of PMMA due to many advantages of this material. PMMA, formed through the polymerizations of methyl methacrylate, is widely known under the commercial names of Plexiglas and Lucite. PMMA can be formed through hot embossing or injection molding. PMMA has an elastic modulus of 3.3 GPA and good optical clarity from the visible into the UV. Other advantages of this material include biological compatibility, gas impermeability and ease of micromachining at relatively low temperatures (−100° C.).

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 1A depicts, in accordance with various embodiments of the present invention, a perspective view of a cartridge;

Figure 1B:
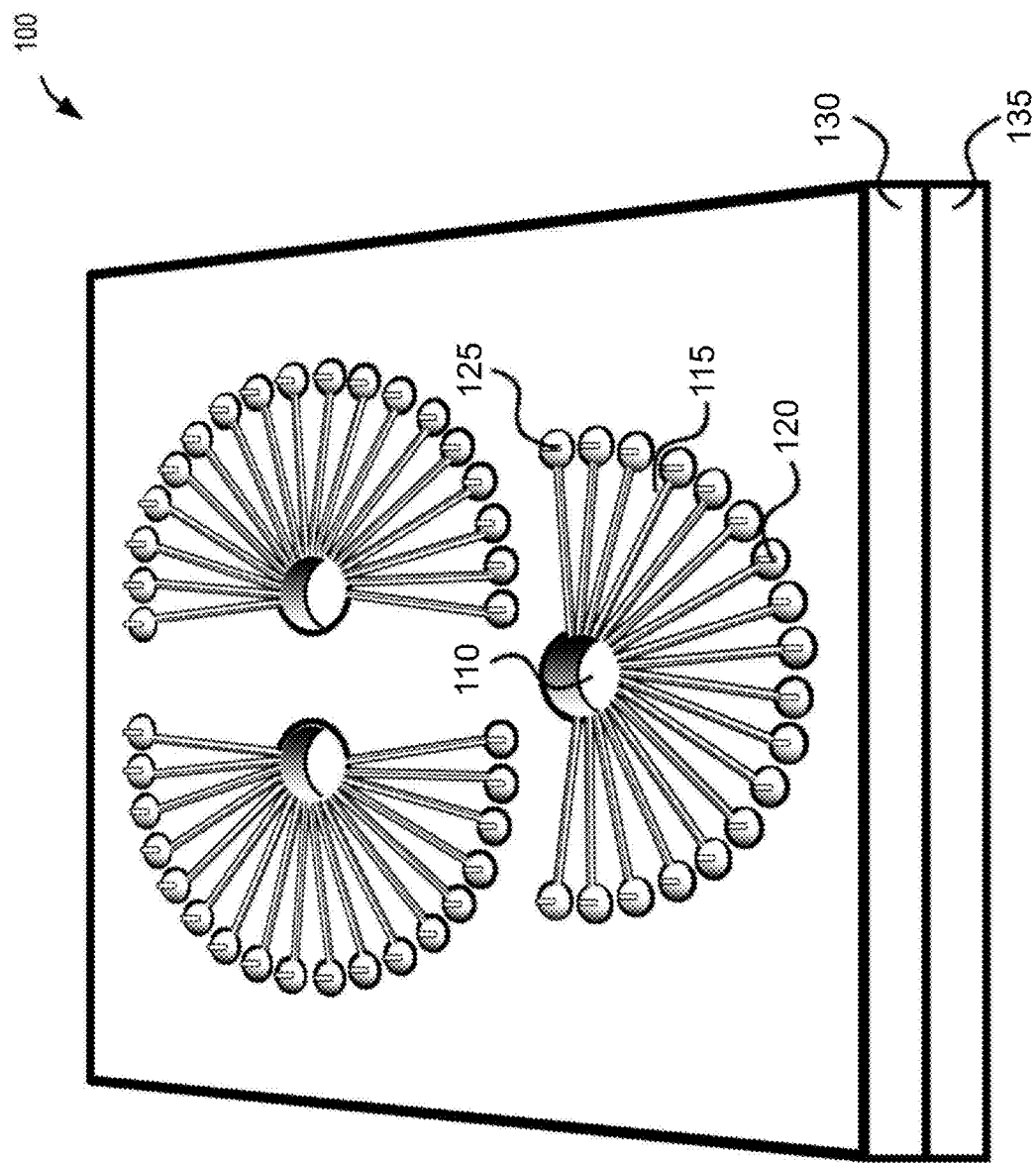
FIG. 1B depicts, in accordance with various embodiments of the present invention, a perspective view of a cartridge.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION

Unless defined otherwise, technical and scientific terms used herein have the same meaning as commonly understood by one of ordinary skill in the art to which this invention belongs. Szycher's Dictionary of Medical Devices CRC Press, 1995, may provide useful guidance to many of the terms and phrases used herein. One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be understood as being modified by the term "about."

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Overview

Therefore, the inventors developed an innovative disposable microfluidic cartridge. In one example, the cartridge can be used either for PCR, LAMP, or other amplification based processes for nucleic acid based detection applications. In some examples, the microfluidic cartridge uses network channels that are angled downwards towards the reaction wells from the inlet ports. Accordingly, once a sample is delivered into the inlet wells, gravity will pull the sample at a downward angle towards the reaction wells and eventually enter the reactions wells.

Additionally, inventors made small (e.g., 0.5 mm or less) ventilation holes positioned directly over and above each reaction wells so that this tiny airflow actually assists in pulling the liquid sample from the inlet well to the reaction wells.

These vent holes also provide an opening to allow a manufacturer to prefill reaction mix and primers set as well. Fortunately, this will allow relatively low trained technicians to operate the device, because as discussed below, they only need to deposit the sample in the cartridge and insert the cartridge into the reader. In old systems, the technician would have to prepare the reaction mixtures themselves at the point of care, and insert them through the inlet well prior to inserting the sample.

Furthermore, the inventors have identified certain materials that optimize the flow using certain channel geometries. For instance, the inventors identified a material that is more hydrophilic than PMMA called Digital ABS (RGD5160-DM) that increased the flow rate of the sample in the channels dramatically.

Accordingly, when PMMA is utilized, angled channels may be necessary for sufficient flow. However, when Digital ABS is used for the cartridge, the channels may not be required to be angled. In these examples, the material will minimize the resistance to flow (e.g. surface tension) sufficiently to allow the sample o flow the reaction wells without as much assistance from gravity as when the cartridge includes angled channels.

FIG. 1 illustrates an example of the cartridge 100 that includes an inlet well 110 for depositing of a sample from a patient (e.g. blood from a finger prick). The cartridge 100 may include top 130 and bottom 135 portions or halves, with the channels and wells being etched or formed in the top surface of the bottom half, and the top half only including access holes/ports above the inlet well 110 and each of the reaction wells 120. Each inlet well 110 may contain many reaction wells 120 connected to it through channels 115. This allows one sample to be tested for several different biomarkers (e.g. one for each reaction well 120 connected to the sample).

Once deposited, the sample flows from the inlet well 110 down channels 115 and into reaction wells 120. The channels 115 are slanted downward so that gravity can pull the sample from the inlet well 110 to the reaction well 120. Additionally, the cartridge 100 has ventilation holes or ports 125 directly above each of the reaction well 120 to release any pressure inside the channels 115 to assist in the flow of the sample down the channel.

Additionally, ventilation ports 125 provide convenient access to pre-deposit reaction chemicals in the reaction wells after fabricating the cartridges 100. Technicians can deposit reaction chemicals directly through the ventilation ports 125 after the entire cartridge is fabricated, without worrying about whether any of the fabrication processes will disturb the pre-reaction mixtures.

The microfluidic cartridge 100 that can be used for many different types of assays including: (1) PCR, (2) LAMP, or (3) other amplification based diagnostic assays. Other suitable microfluidic assays may be performed using the microfluidic cartridge 100. These include but are not limited to fluorescence based detection of DNA, $Ca^{2+}$ and other ions, cell-based assays, colony forming, spectrophotometry assays, transmittance assays, turbidimetry, nephelometry, reflectometry, bioassays, ligand binding assays, immunoassays, enzyme activity assays, and chemilluminiscence.

Figure 2:
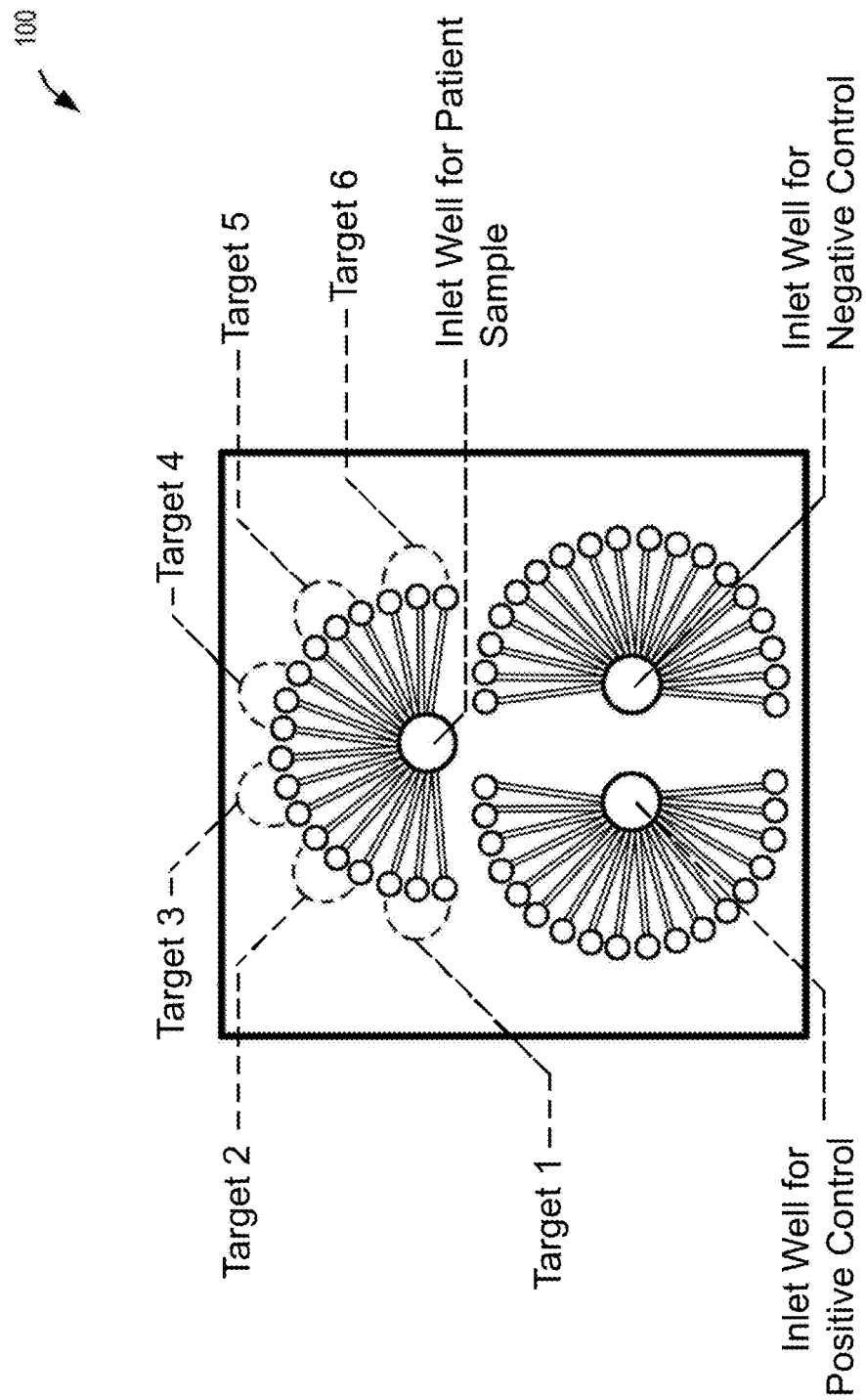
FIG. 2 depicts, in accordance with various embodiments of the present invention, a top view of a cartridge.

FIG. 2 illustrates an example of the layout of a cartridge 100 with three inlet wells 110 that include a patient sample, a positive control inlet well 110 and a negative control inlet well 110. This combination on a single cartridge 100 allows for a quite accurate point of care test to be performed. Additionally, the many network channels 115 connecting the inlet wells 110 to the reaction wells 120 minimizes the amount of times samples need to be applied to the cartridge.

In this case, the clinician only needs to apply a sample to one well 110, and control solutions to the other two wells 110. The channels 115 carry the required liquid to many different reaction wells 120, where the sample or control will be tested for different targets or biomarkers (e.g. DNA of an infectious disease). This minimizes the amount of human and/or sample delivery error introduced into the test results, because for instance, a single sample from the patient is deposited at the same moment. Also, it minimizes the complexity of instructions required for performing the test.

In some embodiments, a single inlet well 110 will be utilized for a sample, and there will only be pre-recorded data for controls. Accordingly, in this embodiment, the clinician would only need to deposit the sample into one well 110.

Reader

Figure 3:
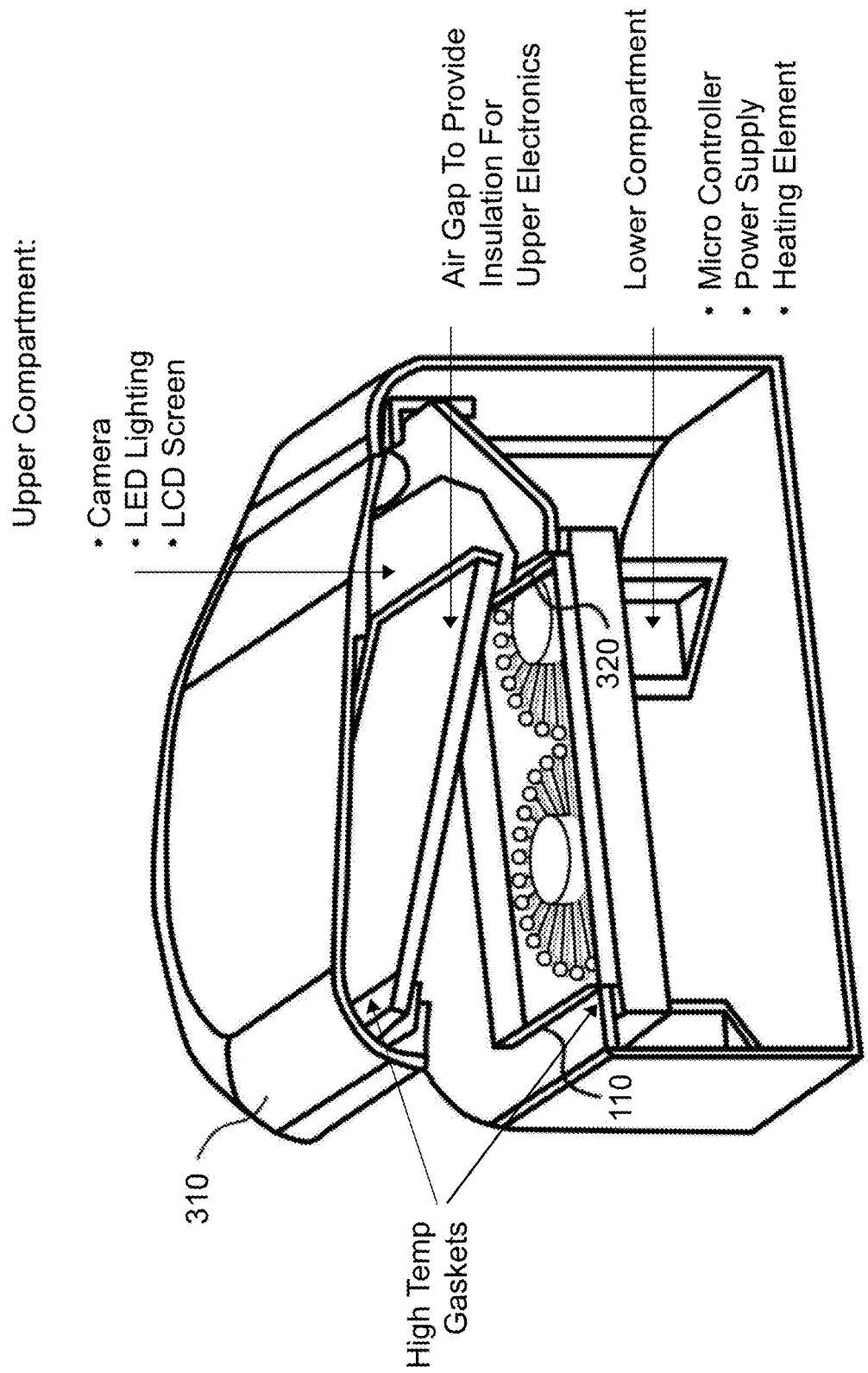
FIG. 3 depicts, in accordance with various embodiments of the present invention, a cross-sectional perspective view of a cartridge reader with a cartridge inside.

FIG. 3 illustrates an example of a device or reader 305 that can read the results from the cartridge 100. A camera or other optical sensor 320 is positioned above or below the cartridge 100 to detect color and or saturation changes in the reaction wells 120 that indicate a positive or negative result.

For instance, for a LAMP reaction, the reader may include a lid 310 with optical sensor 320 and light source. Then, the base 300 may contain a slot or holding component for the cartridge 100 and electronic components including a heater, power supply, and heat control system. For instance, for a LAMP reaction, the heater must undergo heating cycles. Also, for a PCR reaction, the heater must undergo under of heating cycles for the amplification of DNA.

As one example, the control system may include two credit card-sized single-board computers which are Raspberry Pi 2 board (85.60 mm×56 mm×21 mm) and Arduino Uno board (68.6 mm×53.4 mm), and they are placed in the base 300.

A temperature control system may include at least one flexible heating pad for heating the cartridge (or biochip) LAMP reaction zone up to 65° C., and at least one IR digital temperature sensor that is placed on top of the biochip for monitoring the temperature of the LAMP zone. The temperature sensor may be in communication with the temperature controller (e.g., Arduino Uno Board). The relay is incorporated in the device for it is necessary to maintain the temperature at approximately 65° C.

The device may include at least one built-in camera 320 (e.g., Raspberry Pi Camera) that can capture an image after the LAMP reaction to analyze the results. The camera 320 may be configured and arranged to detect the emissions (e.g. fluorescent emissions) from the LAMP zone. The device comprising a plurality of Blue LEDs (e.g, 6 Blue LEDs), and are configured to illuminate the LAMP zone or other reaction zone when they are activated.

The lid 310 may also contain a user interface and/or display for displaying instructions and or the results of the test. For instance, the display may be a 0.98" OLED display configured to display the temperature of the heating of the microfluidic biochip and the ambient temperature inside the device. The system may include a plurality of switch buttons such as: (1) a Chrome Lock Switch for temperature control, a Chrome On Switch for taking an image of the cartridge LAMP zones (e.g. reaction wells 120).

The results of the diagnostic assay may be communicated in several ways. For instance, in some embodiments, LEDs could be used for displaying the results as a simple positive/negative or inconclusive for each of the targets. Additionally, an audio output jack may be configured to announce what type of disease or drug resistance is detected. The device may also include at least one wireless USB WiFi Module that is compatible with Raspberry Pi 2 board to provide a wireless connection for the device. Diagnostic data detected by the reader 305 may be transmitted over a wireless or wired connection through a network to a server for further analysis and/or storage in a database.

Methods for Diagnosing Using Cartridge

Figure 4:
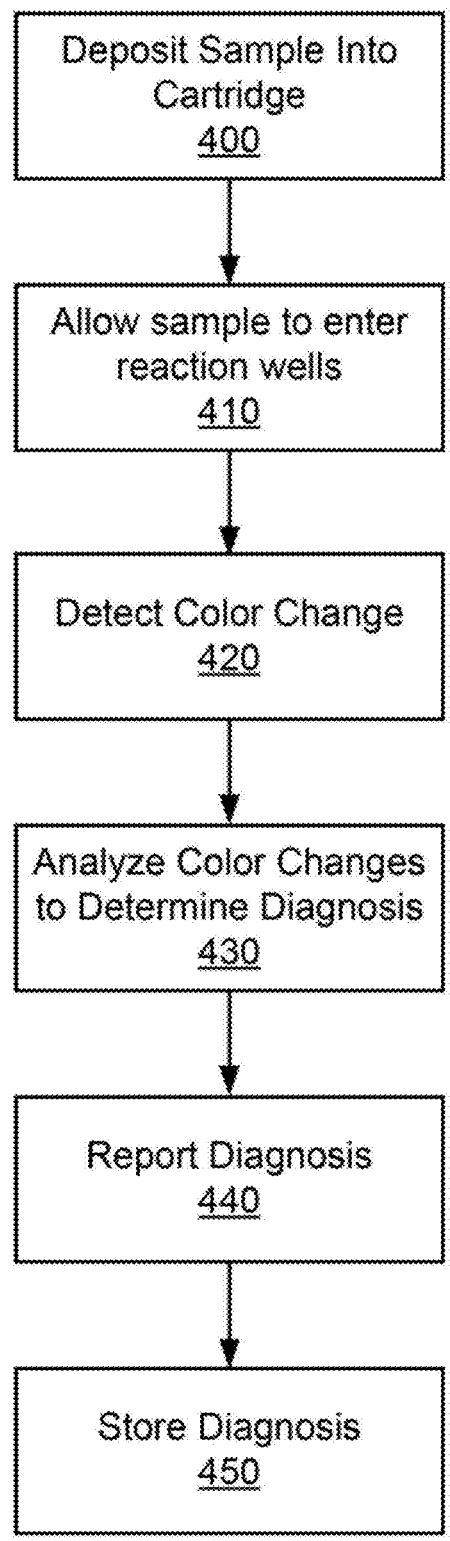
FIG. 4 depicts, in accordance with various embodiments of the present invention, a flow chart illustrating a process for using a cartridge to diagnosis an infectious disease.

FIG. 4 illustrates a method of using the cartridge to diagnose an infectious disease. In the first step, a clinician deposits a sample into an inlet well 110 of the cartridge 400. In some embodiments, a clinician may also deposit control samples into separate inlet wells 110. This will provide quite robust detection, and cancel out any errors due to environmental conditions, etc.

The types of samples deposited may include any that are capable of flowing down the channels to the reaction wells 120. For instance the following samples may be utilized: (1) blood, (2) saliva, (3) sweat, (4) mucous, (5) vaginal swabs, (6) tears, (7) cheek swabs, (8) and others.

In some instances, a sample type with high viscosity or blood clotting (e.g. blood) may be mixed with an anticoagulant or other appropriate solution prior to depositing the sample. In some instances, a solution that decreases the viscosity and/or surface tension may be introduced into the sample. For example, PBS solution can be utilized to dilute blood for sample.

A clinician may deposit the sample 400 using a variety of methods including using a pipette to deposit a standard amount of liquid. In other examples, a syringe could be used to extract blood and deposit it directly. In some embodiments, the sample may be deposited 400 in a tube or column that is placed in the inlet well 110. This will allow gravity to further assist in pushing the liquid of the sample from the inlet well 110 to the reaction wells 120.

After depositing of the sample 400, the clinician must wait for the sample to migrate 410 into the channels 115 and all the way to the reaction wells 120. Accordingly, in some embodiments, the system may utilize a method of determining when the liquid has fully migrated 410, based on image processing. In other embodiments, a clinician may wait to initiate the diagnosis or reading of the cartridge 100 until the clinician observers that the sample (and the controls) have properly entered and sufficiently filled the reaction wells 120.

After the sample has entered the reaction well 410, sufficient time must be allotted for the reaction to take place. For example, if a PCR reaction is being used, sufficient heating and cooling cycles must be completed for the reaction to complete. In some examples, the control indicators will turn color once the reaction is complete. In those cases, the imaging system may utilize those indicators as a time to take an image(s) for diagnostic purposes. For instance, the system could take an image every minute or every five minutes, and once the control color or other optical properties have crossed a threshold, the system could take a picture of the entire cartridge 100 and perform an analysis.

The next step will be to detect color change 420 in each of the reaction wells 120 of the sample. In some cases, this will be compared to the control wells as thresholds or baselines. The color change 420 will depend on the reaction being utilized, and perhaps the fluorescent or other indicator(s) that are tagged to the reaction chemicals. In some embodiments, LED lights or other light sources will be shown on the cartridge 100 by the reader 305, and then an optical sensor 320 will detect fluorescence in a given wavelength range depending on the chemicals used.

In some examples, the color change will be a threshold detection color change 420. This will provide a positive, negative or inconclusive result for each reaction well 120.

Then, after the color change is detected 420 for each reaction well 120, the system may analyze the data for each of the reaction wells 120 to output the diagnosis 440 and/or store the diagnosis 450. In some examples, the results of each of the wells will be pooled into a single diagnosis. Or if multiple tests were performed, a diagnosis for each test may be reported.

For instance, the diagnosis reported 440 may include an indication of whether certain infectious diseases have been detected or the results are inconclusive. In some examples, the well 120 positive/negative data may be displayed on a display connected to the reader 305 and the results may be interpreted by a clinician based on the cartridge 100 installed in the reader 305.

Cartridge

Figure 5:
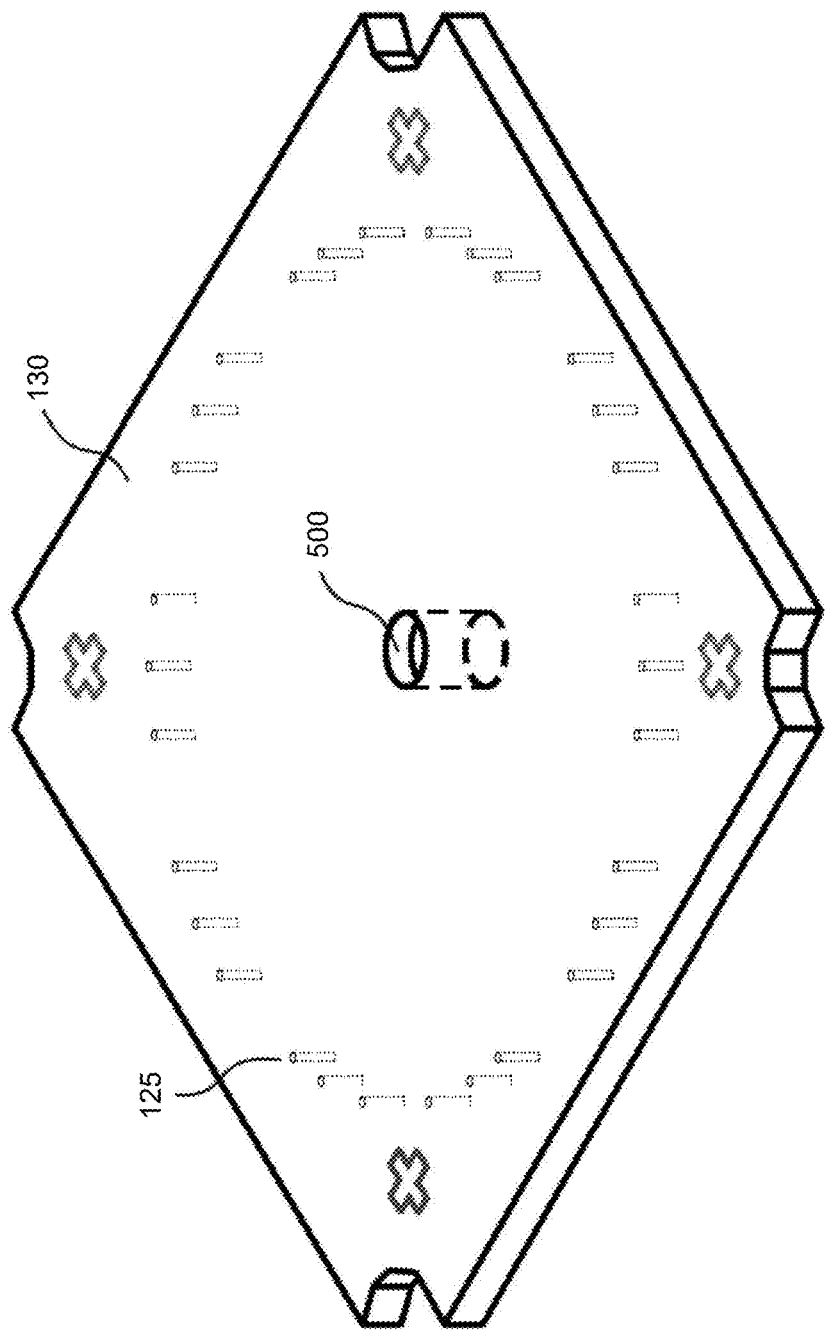
FIG. 5 depicts, in accordance with various embodiments of the present invention, a perspective view of a top half of a cartridge.
Figure 6:
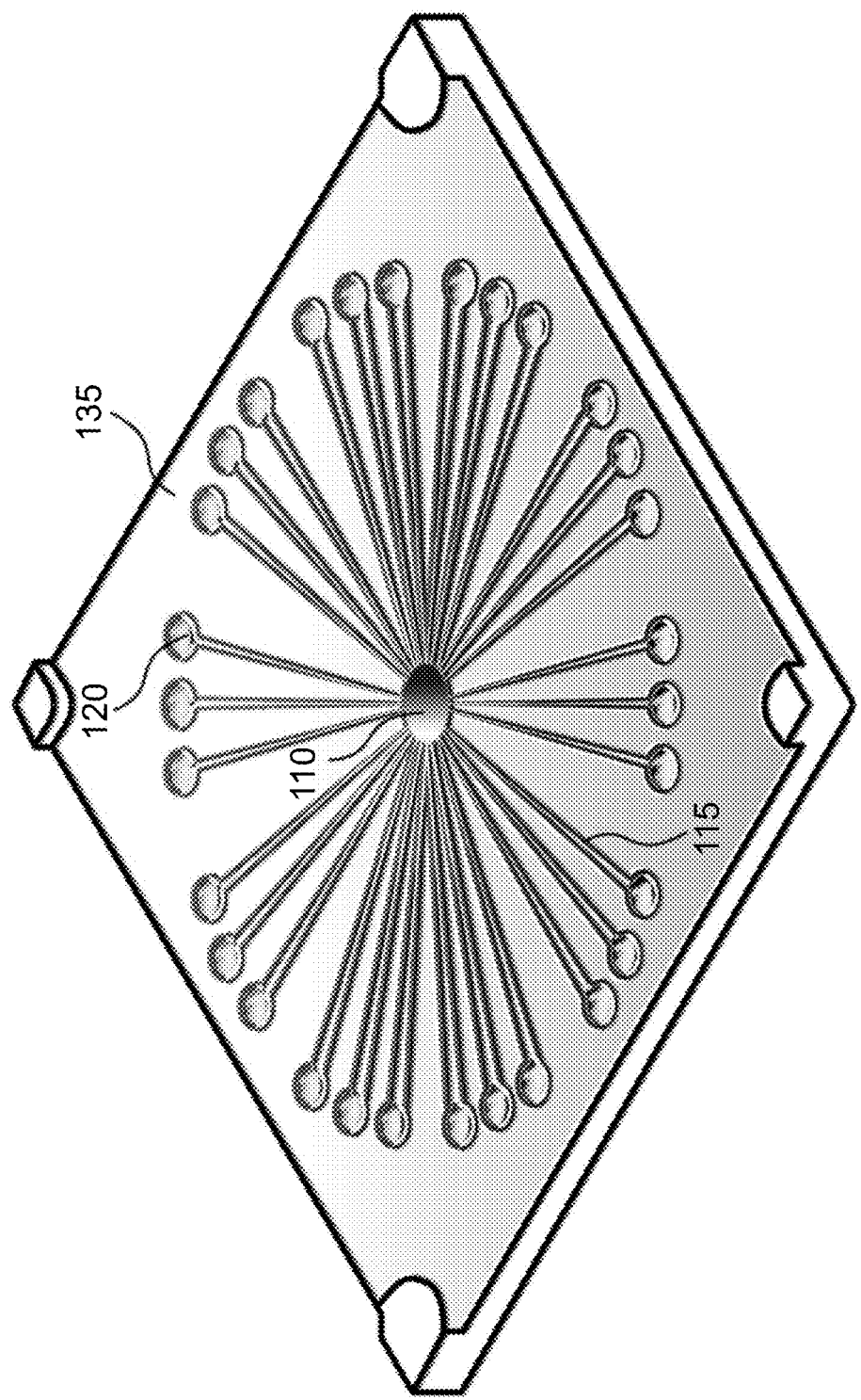
FIG. 6 depicts, in accordance with various embodiments of the present invention, a perspective view of a bottom half of a cartridge.
Figure 7:
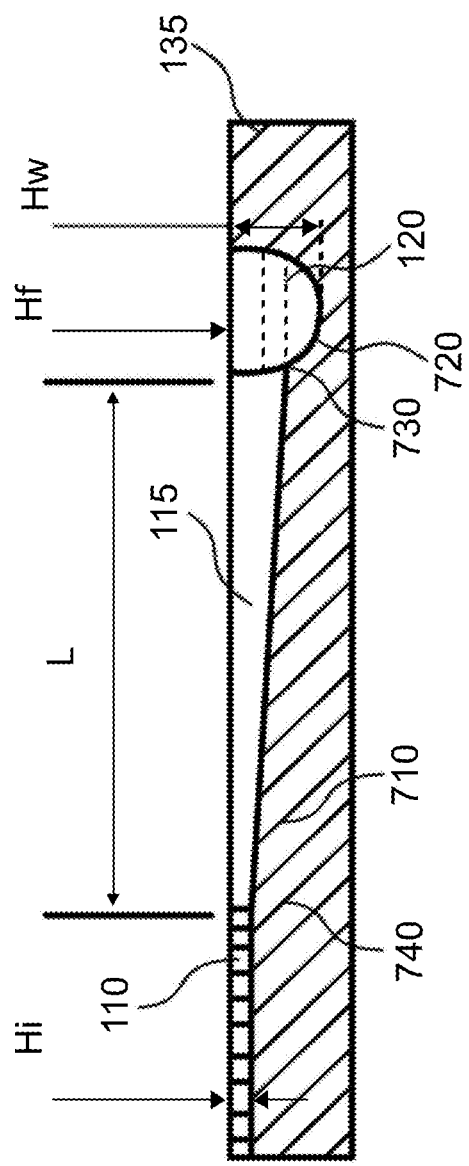
FIG. 7 depicts, in accordance with various embodiments of the present invention, a cross sectional view of a cartridge depicting the inlet well, channel and reaction well.

FIGS. 5-7 illustrate various embodiments of the cartridge 100 that may be utilized to perform the tests disclosed herein. In some examples, the cartridge 100 will have a top portion 130 and a bottom portion 135. In other examples, the cartridge 100 may be manufactured into a single piece.

FIG. 5 illustrates a top portion 130 based on one example of the cartridge 100. As illustrated, the top portion would include at least one inlet well 110, access port 500, and a reaction well 120 access port 125 for each of the reaction wells 120 in the bottom 135 portion. In some examples, the access port 500 will be the same dimensions as the inlet well 110 of the bottom 135 portion.

The access port 500 for the inlet well 110 could be various configurations and geometries, including cylindrical, funnel shaped, and others. The access ports 125 for the inlet wells 110 may be cylindrical or other shapes.

FIG. 6 illustrates an example of the bottom portion of the cartridge 100. As illustrated, the bottom portion 135 includes an inlet well 110, various channels 115, and reaction wells 120 that are in fluid communication with each other. As discussed herein, the sample will be deposited in the inlet well 110 and will flow outward from the inlet well down the channels 115 to the reaction wells 120.

Accordingly, on the bottom portion 135, the inlet well 110 will be a depression, cylinder, or other shaped hole that will allow the sample to be deposited. The cylinder or other shape of the inlet well 110 will all be in fluid communication with the channels 115. The channel 115 entrances from the inlet well 110 may be near the bottom of the inlet well 110. This will insure that all of the sample will drain into the channels 115. In some embodiments, the inlet well 110 may have the shape of a cone on the bottom, or otherwise be raised in the center and taper off to the perimeter of the inlet well 110 to push the sample once deposited to the entrances of the channels 115.

Then, the channels 115 will be connected to the reaction wells 120 and are described further herein. For instance, the channels 115 may radiate outwardly from each of the inlet wells 110, so that the single sample can supply many reaction wells 120. This is also advantageous, because the only opening into the system will be the inlet well 110 and the reaction well 120 access port 125. Accordingly there will be little room for contamination. As illustrated in some embodiments, there will be a single inlet well 110, or multiple inlet wells 110.

The reaction wells 120 may be any suitable shape so that the sample or other testing liquid collects in the reaction wells 120. For instance, the reaction wells 120 may be in the shape of a traditional well with an upside down half spherical depression. In other examples, the reaction will may be an upside down cone. These examples will allow the sample liquid to collect near the center of the reaction wells 120. In some examples, the reaction wells 120 may have a flat bottom in order to evenly distribute the sample liquid.

FIG. 7 illustrates a cross sectional view of a cartridge 100 showing an inlet well 110, a channel 115, and a reaction well 120. As illustrated, an inlet well 110 may have a height "$H_i$," that is constant or increases as it gets closer to the entrance 740 to the channels 115.

Channels 115 may include a floor 710 that is slanted or angled downwards with a particular slope towards the reaction wells 120 along its length ("L"). The slope of the channel floor 710 would be determined by the equation:

$$(H_f - H_0)/L = \text{Slope of Floor 710} \quad (1)$$

Accordingly, the larger the length L of the channels 115 (which allows more reaction wells 120 to be spaced around the inlet well 110) the less the Slope of the Floor will be based on the same $H_i$ if the width of the cartridge is constant. Accordingly, this presents a tradeoff between the thickness of the cartridge, the number of channels 115 and the slope dictates the magnitude of the gravitational force component which will assist the sample in flowing down the floor 710.

In some examples, for a given sample surface tension and viscosity, the angle of the channel floor 710 will need to be great enough so the component of gravity and other capillary forces pulling the liquid down the channels will exceed the repelling force of surface tension and air pressure preventing the flow of the sample down the channels 115. Accordingly, for a more viscous liquid like blood, channels with a greater degree of slant will be required.

As discussed herein, if additives to the sample that do not comprise the test results lower the surface tension and viscosity, the magnitude of the slope of the channel floor 710 may be appropriately decreased. In some examples, different channels 115 will have different slopes to account for different sample types or different cartridge materials 100.

As the surface topography of the inside of the channels 710 and wells is changed, the magnitude of the slope of the channel floors 710 may also be appropriately adjusted to allow for flow to the reaction wells 120. For instance, fluorination or other treatments to the liquid bearing surfaces of the cartridge 100 may be applied to increase or decrease the hydrophobicity of the liquid bearing or contacting surfaces of the cartridge 100. In other cases, plasma cleaning, vinegar, and acid treatments may decrease the hydrophobicity.

Accordingly, the angled or slanted channel floor 710 will allow the sample or other control liquid to flow down the channel 115 and collect in the reaction well 120 without assistance from a pump or vacuum source. This is quite advantageous, because the angle of the slanted channel floor 710 will allow the cartridge 100 to be quite simple, and not require special valves, connections or accompanying pumps. This will allow the construction and manufacturing (discussed below) to be much cheaper and efficient, and will allow the diagnostic assays to be performed with minimal power and equipment requirements.

In some embodiments, the channel floor 710 will be flat, will be shaped like a "V" in a cross section or will otherwise be deeper at the center of the channel. This may reduce flow viscosity at the sides of the channel. In some embodiments, the channel will be "U" shaped to minimize the viscosity.

In some examples, the slope of the channel floor 710 will be constant from the entrance of the channels 740 though the entrance of the reaction wells 710. In other examples, the slope of the channel floor 710 may increase as the channel floor 710 approaches the reaction wells 120, or may decrease as it approaches the reaction wells 120 and other various suitable combinations.

Manufacturing

Figure 8:
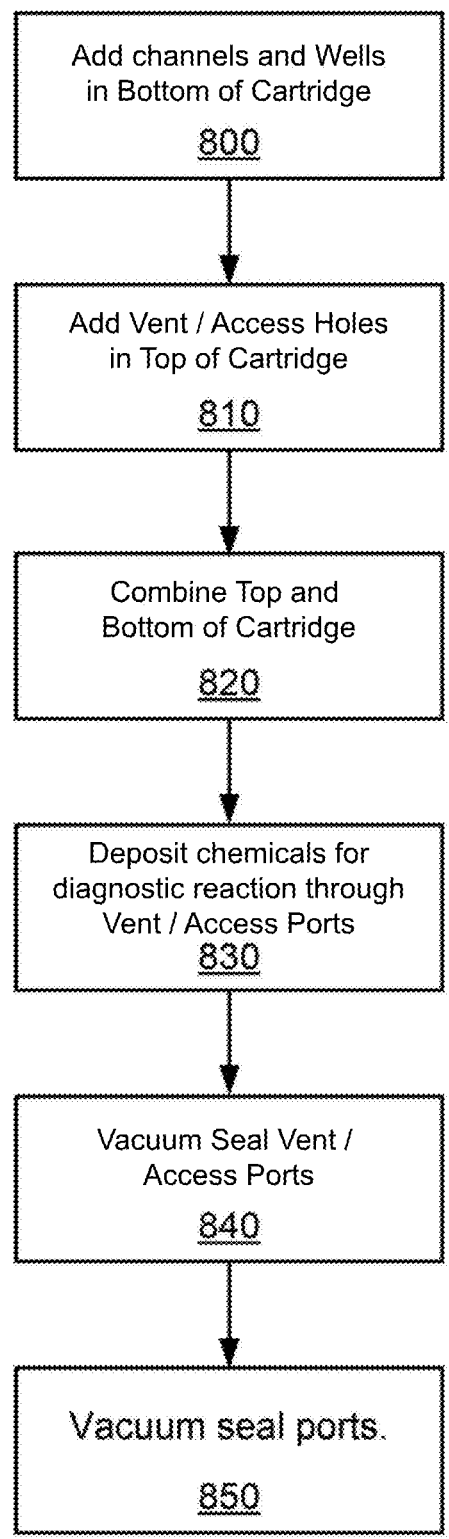
FIG. 8 depicts, in accordance with various embodiments of the present invention, a flow chart of a process for manufacturing a cartridge.

FIG. 8 illustrates an example process for manufacturing the cartridge 100. In some examples, the cartridge 100 may be made of glass or plastic such as silicon, PDMS or PMMA, or other suitable plastics. In some examples the cartridge 100 may be made of several components of plastic sealed together or may be fabricated from one or a couple pieces of plastic. In some examples, the cartridge 100 may be injection molded, stamped, welded, or manufactured using other suitable methods.

For instance, as illustrated in FIG. 8, in some examples the cartridge 100 can be manufactured from two solid pieces of plastic: a top portion 130 and a bottom portion 135. For instance, once a bottom portion 135 is manufactured, the manufacturer will need to add the wells and channels 800 at the specific desired dimensions. In some example, these may be machined onto one side of the bottom portion 135, or may be injection modeled with a form, stamping, 3D printing, micro machining, or other process.

Then, the vent or access ports may be added 810 to the top portion 130. Accordingly, these may be made at various sizes and should be made to line up with the appropriate features on the bottom portion 135.

Then the two halves must be sealed or combined together 820. In some examples, this may involve heat sealing or welding of the two cartridge 100 halves together. Accordingly, this may utilize larger temperatures that would destroy reactants—therefore the reactants will generally be added after the cartridge has been sealed together. In other examples, the two halves may be sealed together using a process that is not heat intensive, and therefore the reactants (e.g. primers) can be pre-deposited in the reaction wells 120 prior to sealing the halves together.

Next, the chemicals, reactants, primers or other required reaction chemicals will be deposited 830 into the reaction wells 120 through the access ports 125. Accordingly, the access ports 125 provide both: (1) ventilation to assist in moving the sample liquid to the reaction wells 120 and additionally provide (2) convenient access to deposit the reaction chemicals after the top 130 and bottom 135 of the cartridge 100 have been sealed together.

Next, after the chemicals are deposited into the reaction wells 120, the cartridge 100 may be sealed 840 over the access ports 125 and inlet wells 110.

Test Kit

Accordingly, the cartridge 100 may be added to a kit that includes, for example: (1) a sealed cartridge, (2) control solutions, (3) pipetting tips other equipment, (4) sample taking devices or storage containers, (5) software for installation into a reader 305 (or may be preinstalled) for the specific cartridge 100, and (6) other chemicals, equipment, or necessary components. The Kit may also include instructions for applying the samples to the cartridge 100, and inserting the cartridge into the reader 305 for reading. Kits may be shipped to the point of use or testing. At that point, the cartridge 100 may be stored until time for testing.

Once a patient is ready for testing, the seal may be removed from the cartridge 100, and a sample may be taken from a patient. Then, the control solutions may be removed from a kit, and the sample and control solutions may be applied to the inlet wells 110 of the cartridge 100. Then (or before applying the samples/solutions) the cartridge 100 may be placed in the reader.

EXAMPLES

The following examples are provided to better illustrate the claimed invention and are not intended to be interpreted as limiting the scope of the invention. To the extent that specific materials or steps are mentioned, it is merely for purposes of illustration and is not intended to limit the invention. One skilled in the art may develop equivalent means or reactants without the exercise of inventive capacity and without departing from the scope of the invention.

Example 1: Tuberculosis

Figure 9:
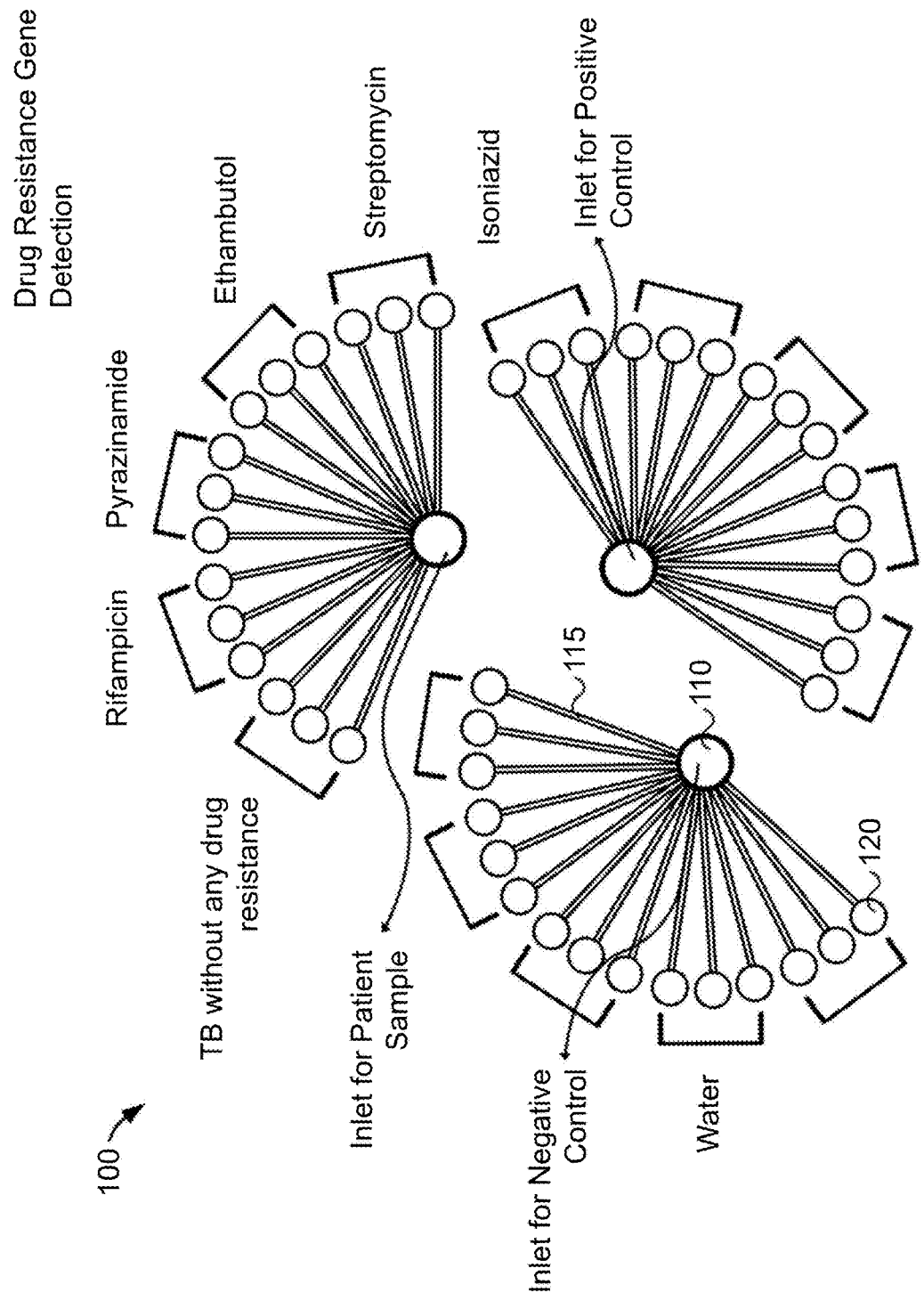
FIG. 9 depicts, in accordance with various embodiments of the present invention, a top view of a cartridge for diagnosing tuberculosis.

FIG. 9 illustrates an example layout for a cartridge used to treat tuberculosis. As illustrated the cartridge 100 contains three inlet wells 110: (1) for positive control, (2) for negative control, and (3) for the patient sample. In this example, the sample inlet well 110 will have channels 115 that link to various reaction wells 120 that include:

Three reaction wells 120 for tuberculosis without drug resistance;
Three reaction wells 120 for tuberculosis with drug resistance to Rifampicin;
Three reaction wells 120 for tuberculosis with drug resistance to Pyrazinamide;
Three reaction wells 120 for tuberculosis with drug resistance to Ethambutol; and
Three reaction wells 120 for tuberculosis with drug resistance to Streptomycin;
Three reaction wells 120 for tuberculosis with drug resistance to Isoniazid;

Accordingly, this will advantageously allow one sample to be tested for tuberculosis, and additionally determine which strain of drug resistant tuberculosis the patient may have. Accordingly, the results would be available at the point of care, and the clinician performing the test, and/or the receiver of the electronic diagnosis could immediately order or prescribe the drug combination necessary to combat that patient's strain of tuberculosis. Accordingly, this avoids multiple rounds of screening and waiting for results to come back from a centralized lab and repeated testing.

This is also critically important, because a point of care test that does not screen for each strain of TB could incorrectly diagnose a patient as having TB but not identifying it has having a drug resistant strain. In that case, if the patient is administered a treatment using a drug the patient is resistant to, the patient can develop extreme resistance to the drug. In that case, the cost of treating a patient can be on the order of $500,000 USD.

The positive and negative control inclusion in cartridge 100 will provide a much higher accuracy and reliability. For instance, if the positive or negative control failed on site, the test could be re-administered with a new cartridge 100. Additionally, unlike point of care tests that do not have positive and negative controls (e.g. pregnancy tests) the system will read color changes and perform comparisons with a much higher degree of accuracy to account for any unique environmental conditions or changes during manufacturing or shipping, etc.

Example 2: Sexually Transmitted Diseases

In another example, a cartridge 100 or a combination of cartridges 100 may contain reaction wells 120 for detecting a plurality of sexually transmitted diseases. In some examples, the STD test will contain inlet wells 110 for samples that contain one or more of the following: (1) saliva, (2) vaginal swab, (3) blood, (4) urine, or other samples. In the example of the vaginal swab, a diluting solution may be added so that the sample may be applied to the cartridge inlet well 110 and flow to the reaction wells 120.

Example 3: Cartridge Materials and Sample Delivery Rates

In a set of experiments, the inventors tested different materials with hydrophilic properties for example cartridges 100 and recorded the resulting flow times. Accordingly, when the entire cartridge 100 is constructed of PMMA, the sample took greater than 60 minutes to flow from the inlet wells 110, through the channels 115 to the reaction wells 120.

However, the inventors identified another material that is more hydrophilic than PMMA called Digital ABS (RGD5160-DM) that increased the speed dramatically. When the inventors applied a sample to a cartridge 100 where the bottom 135 was constructed of Digital ABS (RGD5160-DM), the sample flowed to the reactions wells 120 within a few seconds. Accordingly, the remarkable difference is owed to at least the hydrophilic properties of the material, and the fact that the Digital ABS compound is more porous than PMMA and other materials which reduces the surface tension resistance and increases the flow.

The Digital ABS (RGD5160-DM) is a compound similar to the ABS thermoplastic family from Object Inc., a 3D printer company. The material is named a digital material because it is made from mixing RGD535 and RGD515. RGD525 has a heat deflection temperature of 58-68° C., or 92-95° C. if curing. RGD515 has a melting point of 160° C.

This Digital ABS compound showed to be adapted for the microfluidic device because of its hydrophilic properties, contrary to PMMA that needs additional processes to change the natural hydrophobic surface into a hydrophilic surface. Also, Digital ABS compounds are much more porous than PMMA which also reduces its surface tension.

Accordingly, in some examples the angled channels 115 can be utilized with PMMA, or the digital ABS compounds described above or the Digital ABS compounds described above can be utilized without angled channels 115. In these examples, the flow characteristics will allow sufficient flow in the microfluidic channels 115 that angled channels are not necessary, or only the gravitational pressure from the sample or liquid column inside the inlet well 110 may be sufficient.

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

SELECTED EMBODIMENTS

Although the above description and the attached claims disclose a number of embodiments of the present invention, other alternative aspects of the invention are disclosed in the following further embodiments.

Embodiment 1

A cartridge for performing diagnostic assays, the cartridge comprising:
at least one inlet well comprising an inlet well floor;
a plurality of reaction wells comprising a reaction well floor, wherein each of the reaction well floors are positioned lower than the inlet well floor with respect to gravity; and
a plurality of channels comprising a channel floor connecting the at least one inlet well to each of the plurality of reaction wells, wherein each of the channel floors are angled downward from the inlet well towards the reaction well.

Embodiment 2

The cartridge of embodiment 1, further comprising a plurality of access ports positioned over the reaction wells.

Embodiment 3

The cartridge of embodiment 2, wherein the access ports are cylinder shaped and 0.5 mm in diameter.

Embodiment 4

The cartridge of embodiment 1, wherein the cartridge is comprised of PMMA.

Embodiment 5

The cartridge of embodiment 1, wherein the volume of the inlet well is 200 microliters.

Embodiment 6

The cartridge of embodiment 1, wherein the inlet well is a cylinder that is 3 mm in diameter and 2.34 mm in height.

Embodiment 7

The cartridge of embodiment 1, wherein the inlet well is a cylinder that is 9.2 mm in diameter and 3.175 mm in height.

Embodiment 8

The cartridge of embodiment 1, wherein the inlet well is a cylinder that is 9 mm in diameter and 4 mm in height.

Embodiment 9

The cartridge of embodiment 1, wherein the inlet well is approximately cylinder shaped and has a height of 13 mm and diameter of 3 mm.

Embodiment 10

The cartridge of embodiment 1, wherein the inlet well is cylinder shaped.

Embodiment 10

The cartridge of embodiment 1, wherein the channel floor is angled at the same angle with respect to gravity from the inlet well to the reaction well.

Embodiment 12

The cartridge of embodiment 1, wherein the channel floor is angled at changing angle with respect to gravity from the inlet well to the reaction well.

Embodiment 13

The cartridge of embodiment 1, wherein the angle of the channel floors with respect to gravity is sufficient to overcome the capillary force resisting the flow of fluid from the inlet wells to the reaction wells.

Embodiment 14

The cartridge of embodiment 1, wherein the channel is 10 mm in length, 0.5 mm in height at the entrance to the inlet well, 1.5 mm in height at the entrance to the reaction wells, and 0.5 mm in width.

Embodiment 15

The cartridge of embodiment 1, wherein the channel is 20 mm in length, 0.5 mm in height at the entrance to the inlet well, 1.5 mm in height at the entrance to the reaction wells, and 0.5 mm in width.

Embodiment 16

A cartridge for performing diagnostic assays, the cartridge comprising:
a bottom portion comprising:
at least one inlet well
a plurality of reaction wells in fluid communication with the at least one inlet well, the plurality of reaction wells at a gravitationally lower position than the at least one inlet well to allow liquid to flow from the inlet well to the reaction wells; and
a top portion sealed to the bottom portion, the top portion comprising:
an access port positioned above each of the plurality of reaction wells; and
an access port positioned above the inlet well.

Embodiment 17

The cartridge of embodiment 16, wherein the bottom portion contains three inlet wells.

Embodiment 18

The cartridge of embodiment 16, wherein the bottom and top portion are comprised of PMMA.

Embodiment 19

The cartridge of embodiment 16, wherein the bottom and top portion are injection molded or stamped.

Embodiment 20

A cartridge for performing diagnostic assays, the cartridge comprising:
a cartridge body having a top and bottom, wherein a surface of the bottom is configured to be positioned in a plane that is perpendicular to gravity;
at least one inlet well;
a plurality of reaction wells;
a plurality of channels connecting the at least one inlet well to each of the plurality of reaction wells, wherein a longitudinal axis of the channels is angled downwards from the inlet well towards the reaction wells so that the portion of the channel that is connected to the reaction well is closer to the bottom than the portion of the channel connected to the inlet well.

Embodiment 21

The cartridge of embodiment 20, wherein a flow of the reaction well is lower with respect to gravity than the lowest portion of the channel.

Embodiment 22

The cartridge of embodiment 20, wherein the channels are approximately rectangular shaped.

Embodiment 23

The cartridge of embodiment 20, wherein the surface of the channels include a hydrophobic or hydrophilic coating.

Embodiment 24

The cartridge of embodiment 20, wherein the surface of the channels include a hydrophobic or hydrophilic treatment.

Embodiment 25

A method for diagnosing an infectious disease in a subject, the method comprising:
providing the cartridge of embodiment 1;
depositing a sample from the patient in the at least one inlet well;
allowing the sample to flow into the reaction wells in communication with the inlet well without active flow control;
activating a heater to heat the cartridge for an appropriate amount of cycles for an amplification reaction;
detecting, with a sensor, and optical sensor, light emitted or reflected from the reactions wells and outputting optical data representing the detected light;
sending the optical data to a control system, the control system analyzing the optical data to determine whether the patient has the infection disease; and outputting an indication of whether the patient has the infection disease to a display.

Embodiment 26

The method of embodiment 23, wherein the amplification reaction is a LAMP based reaction.

Embodiment 27

The method of embodiment 23, wherein the amplification reaction is an immunoassay.

Embodiment 28

The method of embodiment 23, wherein the infection disease is tuberculosis.

Embodiment 29

The method of embodiment 26, wherein the indication of whether the patient has the infectious disease comprises whether the patient has tuberculosis and which drugs the strain of tuberculosis is resistant to.

Embodiment 30

The method of embodiment 23, wherein the infection disease is a sexually transmitted disease.

Embodiment 31

The method of embodiment 28, wherein the indication of whether the patient has the infectious disease comprises which of a plurality of sexually transmitted diseases the patient has.

Embodiment 32

The method of embodiment 29, wherein the plurality of sexually transmitted disease comprises at least HIV.

Embodiment 33

A kit for diagnosing an infectious disease, the kit comprising the cartridge of embodiment 1 with reaction primers and reaction mix pre-deposited in the reaction wells.

Embodiment 34

The kit of embodiment 31, further comprising sample preparation solutions, and software to install in a cartridge reader.

Embodiment 35

A method of manufacturing a cartridge, the method comprising:
  providing a top half and a bottom half of the plastic block;
  forming a plurality of inlet wells, reaction wells, and channels in the bottom half of the plastic block
  forming a plurality of access ports in the top half of the plastic block the access ports being positioned so that they will be directly over the inlet wells and reaction wells of the bottom half of the plastic block when the bottom and top half of the block are sealed together; and
  sealing the top and bottom half of the plastic block so that the access ports of the top half are positioned directly over the inlet wells and reactions wells of the bottom half; and
  depositing a reaction mixture in the reaction wells through the access ports.

Embodiment 36

The method of embodiment 33, further comprising sealing the reaction wells after depositing the reaction mixture.

Embodiment 37

The method of embodiment 33, wherein the plastic is PMMA.

Embodiment 38

The method of embodiment 33, wherein the plastic is treated to increase or decrease its hydrophobicity.

Embodiment 39

The method of embodiment 33, wherein the plurality of inlet wells, reaction wells, and channels are coated with a hydrophobic or hydrophilic coating.

Embodiment 40

The method of embodiment 33, wherein the plurality of inlet wells, reaction wells, and channels are treated to increase or decrease the hydrophobicity.

Embodiment 41

The method of embodiment 33, wherein the plastic is a Digital ABS material.

Embodiment 42

The method of embodiment 33, wherein the plastic is a RGD5160-DM.

Embodiment 43

The method of embodiment 33, wherein the plastic is an ABS plastic.

Embodiment 44

The method of embodiment 33, wherein the plastic is an ABS plastic with a hydrophilic treatment.

Embodiment 45

The method of embodiment 33, wherein the plastic is compound comprised of RGD515 and RGD535.

Embodiment 46

A cartridge for performing diagnostic assays, the cartridge comprising:
  at least one inlet well;
  a plurality of reaction wells;
  a plurality of channels comprising a channel floor connecting the at least one inlet well to each of the plurality of reaction wells, and wherein the inlet well, reaction wells, and plurality of channels are comprised of RGD5160-DM.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. A cartridge for performing diagnostic assays, the cartridge comprising:
   at least one inlet well comprising an inlet well floor;
   a plurality of reaction wells comprising a reaction well floor, wherein each of the reaction well floors are positioned lower than the inlet well floor with respect to gravity; and
   a plurality of channels comprising a channel floor connecting the at least one inlet well to each of the plurality of reaction wells, wherein each of the channel floors are angled downward from the inlet well towards the reaction well, and wherein each of the channels comprises a hydrophilic and porous Digital ABS material.

2. The cartridge of claim 1, further comprising a plurality of access ports positioned over the reaction wells.

3. The cartridge of claim 2, wherein the access ports are cylinder shaped and 0.5 mm in diameter.

4. The cartridge of claim 1, wherein the volume of the inlet well is 200 microliters.

5. The cartridge of claim 1, wherein the inlet well is a cylinder that is 3 mm in diameter and 2.34 mm in height.

6. The cartridge of claim 1, wherein the inlet well is a cylinder that is 9.2 mm in diameter and 3.175 mm in height.

7. The cartridge of claim 1, wherein the inlet well is a cylinder that is 9 mm in diameter and 4 mm in height.

8. The cartridge of claim 1, wherein the inlet well is approximately cylinder shaped and has a height of 13 mm and diameter of 3 mm.

9. The cartridge of claim 1, wherein the inlet well is cylinder shaped.

10. The cartridge of claim 1, wherein the channel floor is angled at the same angle with respect to gravity from the inlet well to the reaction well.

11. The cartridge of claim 1, wherein the channel floor is angled at changing angle with respect to gravity from the inlet well to the reaction well.

12. The cartridge of claim 1, wherein the angle of the channel floors with respect to gravity is sufficient to overcome the capillary force resisting the flow of fluid from the inlet wells to the reaction wells.

13. The cartridge of claim 1, wherein the channel is 10 mm in length, 0.5 mm in height at the entrance to the inlet well, 1.5 mm in height at the entrance to the reaction wells, and 0.5 mm in width.

14. The cartridge of claim 1, wherein the channel is 20 mm in length, 0.5 mm in height at the entrance to the inlet well, 1.5 mm in height at the entrance to the reaction wells, and 0.5 mm in width.

15. A cartridge for performing diagnostic assays, the cartridge comprising:

a cartridge body having a top and bottom, wherein a surface of the bottom is configured to be positioned in a plane that is perpendicular to gravity; at least one inlet well; a plurality of reaction wells;

a plurality of channels connecting the at least one inlet well to each of the plurality of reaction wells, wherein a longitudinal axis of the channels is angled downwards from the inlet well towards the reaction wells so that the portion of the channel that is connected to the reaction well is closer to the bottom than the portion of the channel connected to the inlet well, and wherein each of the channels comprises a hydrophilic and porous Digital ABS material.

16. The cartridge of claim 15, wherein a flow of the reaction well is lower with respect to gravity than the lowest portion of the channel.

17. The cartridge of claim 15, wherein the channels are approximately rectangular shaped.

\* \* \* \* \*